United States Patent [19]

Butcher et al.

[11] Patent Number: 5,538,724
[45] Date of Patent: Jul. 23, 1996

[54] METHOD OF CONTROL LEUKOCYTE EXTRAVASATION

[75] Inventors: Eugene C. Butcher, Portola Valley; Philip R. Streeter; Ellen L. Berg, both of Fremont, all of Calif.

[73] Assignee: The Board of Trustees for the Leland Stanford Junior Univ., Stanford, Calif.

[21] Appl. No.: 812,077

[22] Filed: Dec. 19, 1991

Related U.S. Application Data

[63] Continuation-in-part of Ser. No. 717,030, Jun. 18, 1991, abandoned, which is a continuation of Ser. No. 84,490, Aug. 11, 1987, abandoned.

[51] Int. Cl.$^6$ .......................... A61K 39/00; C07K 16/28
[52] U.S. Cl. ........................... 424/152.1; 424/143.1; 424/172.1; 530/388.22; 530/388.75; 530/388.85
[58] Field of Search ............... 424/85.8, 88, 184.1, 424/130.1, 133.1, 158.1, 172.1, 141.1, 143.1, 144.1, 152.1; 530/388.2, 388.22, 388.85, 395, 866, 868, 389.1, 391.1, 391.3; 514/8

[56] References Cited

U.S. PATENT DOCUMENTS 5,403,919  4/1995  Bucher ........................ 530/388.22

FOREIGN PATENT DOCUMENTS 0061141  9/1982  European Pat. Off. ......... C07G 7/00

OTHER PUBLICATIONS

Bevilacqua, M. P. et al., Fed. Proc (FASEB) 46(3):405, abstract 514 (Mar. 1, 1987), "Indentification of an inducible endothelial–leukocyte adhesion molecule (E–LAM 1) using monoclonal antibodies (Mab)".
Butcher, E. C., Current Topics in Microbiology and Immunology 128:85–121 (1986),"The regulation of lymphocyte traffic".
Kohler, G., et al., Nature 256:495–497 (1975), "Continuous culture of fused cells secreting antibody of predefined specificity".
Paul, W. F. (ed), *Fundamental Immunology* (1993), pp. 145, 179–184 and 536–537 only, "Lymphoid tissues and organs".
Rothlein, R., et al., J. Immunology 137:1270–1274 (1986), "A human intercellular adhesion molecule (ICAM-1) distinct from LFA-1".
Jalkanen et al., *Chemical Abstracts*, 107:533 Abstract No. 173820y, (1987). *J. Cell Biol.*,105(2):983–990. Title: Lymphocyte recognition of high endothelium: antibodies to distinct epitopes of an 85–95–kD glyocoprotein antigen differentuially inhibit lymphocyte binding to lymph node, mucosal, or synovial endothelial cells.
Jalkanen et al., *Biological Abstracts*, 83:, Abstract No 34111, (1987). *Eur. J. Immunol*, 16(10):1195–1202 (1986). Title: A lymphoid cell surface glycoprotein involved in endothelial cell recognition and lymphocyte homing in man.
Jalkanen et al., *Biological Abstracts*, 33:, Abstract No. 33106700, (1987). *Cell Differentiation*, 20:120S (1987). Title: An 85–95KDA clycoprotein class is involved in organ-specific homing of human lymphocytes.
Jalkanen et al., *Science*, 223:556–558 (Aug. 1986). Title: A distant endothelial cell recognition system that controls lymphocyte traffic into inflamed synovium.
E. C. Butcher, 1986 Curr. Topics in Microbiol. and Immunol. pp. 85–121.
E. C. Butcher, et al. 1979 J. Immunol. 123(5): 1996–2003, Lymphocyte adherence.

*Primary Examiner*—Kay K. A. Kim
*Assistant Examiner*—Thomas Cunningham
*Attorney, Agent, or Firm*—Bertram I. Rowland

[57] ABSTRACT

Methods and compositions are described for modulating trafficking of leukocytes to endothelial cells involving the binding of homing receptors and addressins. Particularly, compositions are provided which can inhibit the interaction between the homing receptor and addressin or provide for directing specific molecules associated with diagnosis or treatment, where the molecules bind to the addressins.

6 Claims, No Drawings

METHOD OF CONTROL LEUKOCYTE EXTRAVASATION

REFERENCE TO GOVERNMENT GRANT

The United States government has rights to this invention pursuant to Grant No. GM-37734, awarded by the National Institutes of Health.

CROSS REFERENCE TO RELATED APPLICATIONS

This application is a continuation-in-part of application Ser. No. 717,030, filed Jun. 18, 1991, now abandoned, which is a continuation of application Ser. No. 084,490, filed Aug. 11, 1987, now abandoned.

INTRODUCTION

1. Technical Field

The field of this invention is the trafficking of leukocytes as directed by homing receptors, addressins and selections.

2. Background

Leukocytes, which include lymphocytes, monocytes and other myeloid cells, are continuously circulating by means of the bloodstream and in the case of lymphocytes, the lymphatic vessels as well. In the case of the lymphocytes, the lymphocytes recirculate in moving from the bloodstream into lymphoid organs, then to the collecting efferent lymphatics and eventually back to the bloodstream, where they re-enter the cycle.

Lymphocytes have the remarkable capacity to recognize and bind selectively to specialized endothelial cells in lymphoid organs and sites of inflammation, binding initially to the luminal surface and then migrating through the vessel wall into the surrounding tissue. Outside of the spleen, such migration occurs through post capillary venules in lymph nodes and Peyer's patches and in sites of chronic inflammation. These vessels are often characterized by distinctive plump endothelial cells and thus are referred to as "high endothelial venules," or HEV.

The trafficking of lymphocytes has both positive and negative aspects. On the positive side, the lymphocytes migrate to sites of inflammation or damage, where the lymphocytes may serve to counteract infectious agents, aid in the rehabilitation of the tissue, and the like. On the other hand, the lymphocytes may be participants in enhancing inflammation, as is observed in autoimmune diseases, tissue injuries, ulcers, and the like.

Neutrophils are also involved in trafficking to sites of inflammation. Neutrophils have been implicated in reperfusion injury, autoimmune diseases, and the like.

The ability to regulate the trafficking of the leukocytes, so as to enhance trafficking of the leukocytes to certain sites as well as inhibiting trafficking to other sites could be of therapeutic importance. By being able to modulate the trafficking of leukocytes to sites of injury, where the presence or absence of such cells is desired, one may be able to enhance healing or prevent injury by virtue of the presence of such cells.

RELEVENT LITERATURE

The interaction of lymphocytes with HEV has been studied in an in vitro model by Stamper and Woodruff (1976) *J. Exp. Med.* 144:828–833; Jalkanen and Butcher (1985) *Blood* 66:577–582; Butcher (1986) *Curr. Topics Microbiol. Immunol.* 128:85–122; and Butcher et al. (1979) *J. Immunol.* 123:1996.

Reports concerning homing receptors may be found in Gallatin et al., (1983) *Nature* 304:30–34; Jalkanen et al. (1986) *Eur. J. Immunol.* 16:1195–1202 and Butcher *Curr. Topics Microbiol. Immunol.* (1986) 128:85, who describe Mel-14 and Hermes-1. Kishimoto et al., (1990) *Proc. Natl. Acad. Sci. USA* 87:2244–2248 describe antibodies which inhibit binding of lymphocytes to HEV. See also Lewinsohn et al. (1987) *J. Immunol.* 138:4313–4321. Berg, et al., (1991) *J. Cell Biol.* 114:343–349 describe the human peripheral lymph node vascular addressin for LECAM-1. Picker et al., (1990) *Am. J. Pathology,* 1366:953–1067, Picker, et al., (1991) *Nature* 349:796–799 describe ELAM-1 as an adhesion molecule for skin-homing T cells.

SUMMARY OF THE INVENTION

Compositions and methods are provided for modulating the ability of leukocytes to extravasate through endothelial walls by affecting the ability of the leukocytes to bind to surface membrane proteins (addressins) of endothelial cells by controlling binding between homing receptors and addressins. Particularly, molecules are employed, proteinaceous, carbohydrate, or combinations thereof, which can serve as antagonists to inhibit the binding of leukocyte surface membrane proteins (homing receptors) to surface membrane proteins of endothelial cells (addressins). Particularly, one can modulate binding to endothelial cells associated with mucosal tissue (e.g., Peyer's patches), lymph node, synovium, skin, or other lymphoid-related or inflamed tissue. The use of these antagonists finds application in the treatment for a wide variety of diseases and immunological disorders. In addition, compounds binding to the endothelial surface membrane proteins may serve to direct a variety of reagents to the endothelial sites.

DESCRIPTION OF THE SPECIFIC EMBODIMENTS

Compositions and methods are provided for binding to surface membrane proteins of endothelial cells, where binding of leukocytes to such surface membrane proteins can result in extravasation of the leukocytes to a site outside of the blood vessels, usually sites of inflammation. The surface membrane proteins, referred to as addressins (or endothelial cell (EC) ligands) may be up-regulated in association with inflammation. In many instances, recruitment of leukocytes to a particular site may be associated with disease. In addition, there may be interest in directing specific agents to a site associated with extravasation. The compounds of this invention are associated with modulating binding, i.e., binding to or inhibiting binding of endothelial surface membrane proteins, such as addressins with leukocyte ligands.

The addressins may be associated with endothelial cells associated with a variety of tissues, particularly lymphoid tissue or tissue at sites of inflammation, where the tissue may be mucosal, peripheral lymph node, mesenteric lymph node, Peyer's patch, synovium, appendix, cutaneous or other tissue e.g., squamous epithelium. The endothelial cells are normally associated with post-capillary venules, e.g., high endothelial venules (HEV), where the presence of the addressins allows particular subsets of leukocytes, particularly lymphocytes, to bind to the post-capillary venules and be transported by diapedesis to an extravascular site. Three vascular addressins for lymphocytes are identified as the peripheral lymph node addressin (PNAd) which is selectively expressed in peripheral lymph node HEV; the mucosal addressin (MAd) expressed by HEV in mucosal lymphoid organs, such as Peyer's patches and appendix; and a skin vascular addressin, ELAM-1, which during chronic inflammation is expressed preferentially by venules in the skin and appears to regulate the traffic of a skin-specific memory lymphocyte population to this site. ELAM-1 is also associated with trafficking of neutrophils.

The mucosal addressin (MAd) is a glycoprotein of about 58–66 kDa. It contains sialic acid which appears to be O-linked, as it is not sensitive to peptide N-glycosidase. Isolated MAd, incorporated into artificial planar lipid membranes, avidly binds lymphocytes and mucosal HEV-binding cell lines. In addition to Peyer's patches and mesenteric lymph nodes, MAd is found also on the gut lamina propria, mammary gland, and occasionally small vessels in the pancreas and a thin layer of cells lining the marginal sinus around splenic white pulp nodules in the spleen. MAd is not detectable on endothelium in non-mucosal sites of acute inflammation, nor in cutaneous CFA-induced chronic granulomas, but may be found within chronically inflamed pancreas of non-obese diabetic mice, as well as in endothelial venules in the central nervous system during relapsing episodes of chronic experimental allergic encephalomyelitis, an animal model for myasthenia gravis. MAd is found to bind to monoclonal antibodies MECA-367 and -89 (Streeter et al. (1988) *Nature* 331:41–46).

The peripheral lymph node addressin (PNAd) comprises a number of glycoproteins, including prominent species of about 50–60 kDa and other species of about 90–100 kDa. The addressin is found in peripheral lymph nodes, tonsils, some sites of extralymphoid chronic inflammation and some mucosal lymphoid tissues. The antibody MECA-79 binds to the PNAd. (Streeter et al. (1988) *J. Cell. Biol.* 107:1853–1862). The addressin appears to be a glycoprotein, but may also comprise other glycoconjugates where MECA-79 may bind to the carbohydrate portion of the molecule.

The skin vascular addressin ELAM-1 (endothelial-leukocyte adhesion molecule-1) is an about 115 kDa glycoprotein. ELAM-1 is involved in the adhesion of neutrophils to cytokine-activated human umbilical vein endothelial cells in vitro and is rapidly induced on such cells by IL-1, TNFα, LPS and on a subset of venules in sites of acute inflammation in vivo (Cotran (1986) *J. Exp. Med.* 164:661–666; Bevilacqua et al. (1987) *Proc. Natl. Acad. Sci. USA* 84:9238–9242; and Pober et al. (1986) *J. Immunol.* 136:1680–1687. ELAM-1 expression is also found on venules in settings dominated by mononuclear cell influx, especially skin sites of chronic inflammation and in some extra-cutaneous sites of chronic inflammation (Picker et al. (1991) *Nature* 349:796–799).

The addressins may be from any mammalian source, particularly primate, more particularly human, although the addressins concerned with this invention may be from domestic animals, wild animals, and the like from species such as canine, ovine, bovine, equine, feline, murine, etc.

The ability to inhibit immune system functions is known to be therapeutically useful in treating diseases such as allergies, autoimmune disease including rheumatoid arthritis and systemic lupus erythematosus, certain types of kidney diseases, inflammatory lung diseases such as idiopathic pulmonary fibrosis and hypersensitivity pneumonitis, certain types of endocrinological diseases such as Grave's disease or early diabetes, and certain types of cardiac disease such as rheumatic fever. Immunosuppression is also therapeutically useful in preventing the harmful immune "rejection" response which occurs with organ transplantation or in transplantation of bone marrow cells used to treat certain leukemias or aplastic anemias. According to the invention, tissue specific immunosuppressive therapies for these and other types of diseases are provided. Some of these diseases are listed below in Table 1.

TABLE 1

EXAMPLES OF
DISEASES OR IMMUNOLOGICAL DISORDERS

Autoimmune and Related Disorders

Systemic Lupus Erythematosus
Rheumatoid Arthritis
Polyarteritis Nodosa
Polymyositis and Dermatomyositis Progressive systemic
Sclerosis (Diffuse Scleroderma) Glomerulonephritis
Myasthenia Gravis Sjogren's Syndrome Hashimoto's Disease
and Graves' Disease Adrenalitis, Hypoparathyroidism, and
Associated Diseases
Pernicious Anemia
Diabetes Multiple Sclerosis and Related Demyelinating
Diseases Uveitis Pemphigus and Pemphigoid Cirrhosis and
Other Diseases of the Liver Ulcerative Colitis S
Myocarditis
Local Manifestations of Drug Reactions (dermatitis, etc.)
Inflammation-Associated or Allergic Reaction Patterns of the Skin Atopic Dermatitis and Infantile Eczema
Contact Dermatitis Psoriasis Lichen planus
Allergic enterodathies
The Atomic Diseases Allergic Rhinitis
Bronchial Asthma
Transplant Rejection (heart, kidney, lung, liver, pancreatic islet cell, others)
Hypersensitivity or Destructive Responses to Infectious Agents Poststreptococcal Diseases (e.g. Cardiac manifestations of rheumatic fever)
Others Another aspect of the invention is the targeting of therapeutic or diagnostic reagents (radiotoxins, reagents capable of inducing vascular permeability to enhance access of soluble blood-borne macromolecular reagents to surrounding tissues or neoplasms, or radiologic, nuclear magnetic resonance or other imaging reagents) to specific tissues or organs. Reagents are covalently linked, using conventional techniques, to antibodies or other specific binding molecule to tissue-specific endothelial cell ligands or molecules, and injected intravenously to localize along the vasculature in the target organ or tissue. Such targeting allows novel imaging approaches to the diagnosis of vascular abnormalities or to the evaluation of the vascularization of malignancies. For example, since tissue-specific endothelial cell ligands may be induced inappropriately by factors produced locally by metastatic cells (for instance, mammary gland tissue induces mucosal endothelial ligands locally, and metastatic breast carcinoma might therefore induce mucosa-specific endothelial molecules as well) imaging reagents injected intravenously might readily identify sites of metastatic breast carcinoma. This approach to imaging of neoplasms, based on changes in the surface of endothelial cells in the local vasculature, avoids the problem of delivery of macromolecules to extravascular sites. The invention also permits localized targeted delivery of therapeutic agents to selective tissues or organs.

All inflammatory and immune responses in tissues require absolutely the presence of leukocytes at the site(s) of inflammation. The leukocytes include lymphocytes and their progeny, monocytes, neutrophils, eosinophils, basophils, natural killer cells, and/or mast cells. All such leukocytes originate in the bone marrow, travel through the blood, and only enter tissue sites where they can contribute to immune responses by interacting with and migrating between blood vessel endothelial cells. The ability to prevent leukocyte extravasation into particular organs or tissues therefore provides an effective but tissue-selective immunosuppressive therapy. The present invention permits the targeted inhibition of lymphocyte and leukocyte entry into mucosal lymphoid and inflammatory tissues, into lymph nodes, into synovium and skin, and by extension into other discrete organs such as brain, heart, kidney, lung and liver. The method of the invention therefore provides a preferable mode of immunosuppressive therapy for localized diseases in which inflammatory or immune reactions contribute to pathology.

The compositions for modulating the binding of the homing receptor to the addressin may be varied. Thus, soluble forms of the addressin may serve to bind to the homing receptor and inhibit binding of the homing receptor to the addressin, where the soluble form may be a protein or fragment thereof, a carbohydrate, glycoprotein, or other molecule capable of mimicking a portion of the addressin which binds to the homing receptor. These proteins may include sequences having the same or substantially the same sequence as the addressin, anti-idiotypes where the anti-idiotype binds to an antibody which binds to the addressin, carbohydrate portions of the addressin which bind to a lectin portion of homing receptors, and the like. Alternatively, one may use antibodies which bind to the addressin, where the antibody binds at a site which interferes with the binding of the homing receptor to the addressin. The antibodies may be polyclonal or monoclonal. Monoclonal antibodies may be made in accordance with conventional ways and may be derived from a wide variety of sources, which include murine, lagomorpha, bovine, ovine, and the like.

For targeting various molecules to post-capillary venules, specific binding molecules, ligands or antibodies will be employed which bind to the addressin. It is not necessary that the specific binding molecules interfere with the binding of the homing receptor to the addressin, all that is required is binding to the addressin. The ligands may include carbohydrates which specifically bind to the addressins. The carbohydrate molecules will mimic the sugar portion of the homing receptor glycoprotein which binds to the addressin. The sugar molecule may be totally carbohydrate or may have a peptide of fewer than 50, and usually fewer than 30, amino acids. Thus, by hydrolyzing the glycoprotein homing receptor, one may obtain fragments which have at least 25%, usually at least 50% and preferably at least 75% by weight of carbohydrate. By determining the structure of the sugar, one may synthesize the sugar by conventional ways.

The peptides which are employed for binding to the homing receptor, will usually be at least eight amino acids, more usually at least 12 or 16 amino acids, and preferably at least about 20 amino acids. Various techniques may be employed to extend the lifetime of the smaller peptides, by using an unnatural amino acid as part of the chain, where the unnatural amino acid does not affect the binding conformation of the peptide, by employing liposomes, by modifying the molecule with stabilizing molecules, such as polyethylene glycol, or the like. The molecules may be administered by any convenient means, particularly parenterally, more particularly intravascularly.

The antibodies used in the method of the present invention are preferably administered to individuals, preferably mammals, in a manner that will maximize the likelihood of the antibody reaching the targeted endothelial cell, binding to it, and thereby blocking the binding of circulating lymphocytes. This in turn will inhibit or divert lymphocyte traffic through particular sites and thus control certain neoplastic or dysfunctional lymphoid diseases, such as those identified in Table 1. As indicated above, carbohydrates may find use to act as inhibitors, or other molecules which specifically bind to the addressin. Of particular interest is retaining a portion of the peptide portion of the homing receptor in conjunction with the sugar.

The dose for individuals of different species and for different diseases is determined by measuring the effect of the antibody on the lessening of those parameters which are indicative of the disease being treated. Being proteins, the antibodies will normally be administered parenterally, preferably intravenously. In a mouse model for local inflammatory disease (e.g., intestinal hypersensitivity response), a dose of MECA-367 antibody of 0.5–2 mg/host/week for 2 weeks would be sufficient to reduce inflammation of the disease. The dose of the antibody may have to be repeated periodically depending on the particular disease. Moreover, the effects of many autoimmune diseases are considered irreversible, e.g., the collagenization in sarcoidosis, or the terminal effects of prolonged rheumatoid arthritis. Thus, treatment of the susceptible individual will be prior to terminal manifestation of the disease, and possibly prior to the onset of the disease. Whether or not a disease is fully manifested may be determined by monitoring clinical symptoms, as well as the presence of specific antibodies associated with the autoimmune disease.

When administered parenterally the antibodies will be formulated in an injectable dosage form (solution, suspension, emulsion) in association with a pharmaceutically acceptable parenteral vehicle. Such vehicles are inherently nontoxic and nontherapeutic. Examples of such vehicles are water, saline, Ringer's solution, dextrose solution, and Hanks' solution. Nonaqueous vehicles such as fixed oils and ethyl oleate may also be used. The vehicle may contain minor amounts of additives such as substances that enhance isotonicity and chemical stability, e.g., buffers and preservatives. The antibody is preferably formulated in purified form substantially free of aggregates and other proteins at concentrations of about 1 to 50 mg/ml.

For arthritis, local administration may be particularly effective, using means of subcutaneous implant, staples or slow release formulation implanted directly proximal the target. Slow-release forms can be formulated in polymers, such as Hydron (Langer, R., et al. (1976) *Nature* 263:797–799) or Elvax 40P (Dupont) (Murray, J.B., et al. (1983) *In Vitro* 19:743–747). Other sustained-release systems have been suggested by Hsieh, D.S.T., et al. (1983) *J. Pharm. Sci.* 72:17–22). Suitable pharmaceutical vehicles and their formulations are described in Remington's Pharmaceutical Sciences by E.W. Martin which is incorporated herein by reference.

The following examples further illustrate the invention. These examples are not intended to limit the scope of the invention. In light of the present disclosure, numerous embodiments within the scope of the claims will be apparent to those of ordinary skill in the art.

EXPERIMENTAL

Peripheral Lymph Node and Mucosal Addressins

Antigen source: From functional studies of lymphocyte-endothelial cell interactions in vivo and in vitro, it has been shown that lymph node HEV are specialized in their expression of functionally defined tissue specific ligands for lymphocyte homing receptors. Furthermore, the HEV in mesenteric lymph nodes are known to bind both lymph node-specific and mucosal HEV-specific cell lines. Thus, in order to produce antibodies against peripheral lymph node-specific and mucosal lymphoid specific endothelial cell (addressin) ligands, a crude pooled preparation containing high endothelial venules from peripheral and mesenteric lymph nodes was used.

Brachial, axillary, inguinal, and mesenteric lymph nodes from BALB/c mice were pooled in Hank's balanced salt solution (HBSS), minced, and gently pressed between glass microscope slides to release lymphocytes. The resulting cell suspension was then passed through Nitex mesh (Sullivan's, San Francisco, Calif.), and the stromal elements which remained on top of the mesh were collected. These stromal preparations were treated for 10 minutes with HBSS containing 0.32 mg collagenase/ml (5 ml/mouse), washed, and again passed through Nitex. The stromal cells remaining on the Nitex were collected, suspended in HBSS, and used for immunization.

Immunization protocols: For the fusion which led to the generation of MECA-89, a Wistar rat received three intraperitoneal (i.p.) priming doses of lymph node stroma (from 3 mice/injection) mixed with precipitated aluminum potassium sulfate (adjuvant/carrier) in a 3:2 ratio, final volume 1 ml. These immunizations were given two to three weeks apart, and 17 days after the third priming dose, the rat was boosted i.p. with stromal cells (from 10 mice) in HBSS.

For the fusion which led to the generation of MECA-367 and MECA-79, approximately $1 \times 10^8$ spleen cells from the animal used for the MECA-89 fusion were adoptively transferred to a normal Wistar rat. On the day following cell transfer, and again two months later, this animal was immunized with lymph node stroma (from 5 mice/injection) mixed with precipitated aluminum potassium sulfate. One week after this second immunization, the rat was boosted i.p. with a stromal cell preparation (from 10 mice) in HBSS.

Hybridoma production: Three (MECA-89 fusion) to four (MECA-367/MECA-79 fusion) days after final boosts, rat spleen cells were mixed with the mouse myeloma Sp2/O (ATCC HB American Type Culture Collection, Rockville, Md.), at a lymphocyte to myeloma ratio of two to one, and fused using polyethylene glycol 4000, gas chromatography grade (EM Science, West Germany). Hybrid cells were selected for their ability to grow in RPMI 1640 medium (JR Scientific) containing hypoxanthine, aminopterin, and thymidine (Kohler and Milstein, *Nature*, supra).

Monoclonal antibody screening: Screening of monoclonal antibodies was carried out as follows:

1. Initial immunohistologic selection by immunofluorescence: Hybridoma supernatants were screened for the presence of monoclonal antibodies recognizing endothelial cells, in particular lymphoid tissues and inflammatory sites. Lymphoid and in some cases extralymphoid tissues were embedded in Tissue Tek OCT compound (Lab-Tek Products) and frozen on dry ice. 8–12 μm thick frozen sections were cut and fixed by 2 to 10 minute immersion in cold acetone, and allowed to air dry. The sections were covered with 50–100 μl of hybridoma supernatant, incubated 10 minutes, and washed by immersion 5 minutes in HBSS. Slides were then incubated for 10×5 minutes at room temperature in Coplin jars containing a 1:20 dilution of second-stage antibody, FITC-conjugated goat anti-rat IgG (Sigma) in HBSS containing 5% normal mouse serum. Slides were washed in HBSS, and examined by fluorescence microscopy. Supernatants containing antibodies reactive with high endothelial venule cells in lymph nodes and/or in Peyer's patches, were selected for cloning by limiting dilution.

Additional immunohistologic staining was carried out by immunoperoxidase staining. Acetone-fixed frozen sections (6–12 μm thick) of various lymphoid and extralymphoid tissues were incubated with purified monoclonal antibody in phosphate buffered saline (PBS), washed, and treated with a solution of horseradish peroxidase conjugated rabbit anti-rat IgG (DAKO, Copenhagen, Denmark; used at 1:40), 5% normal mouse serum, and PBS. The horseradish peroxidase conjugated second antibody was detected following exposure to a solution of diaminobenzidine and $H_2O_2$, and the staining was enhanced by incubation in 0.5% copper sulfate in saline. Sections were lightly counterstained with hematoxylin.

Hybridomas producing antibodies that stained HEV in a tissue-selective manner were subcloned by limiting dilution, and stable clones were frozen in liquid nitrogen for storage. These included MECA-89 and MECA-367, specific for HEV in mucosa-associated tissues; and MECA-79, which preferentially stains lymph node HEV and recognizes Peyer's patch HEV only weakly or focally.

Aliquots of the subcloned hybridomas were adapted for growth in HB101 serum free medium (New England Nuclear) and grown in bulk for production of monoclonal antibodies. Immunoglobin in the resulting culture supernatant were precipitated by addition of ammonium sulfate to 50% saturation, and the yield and purity of monoclonal antibodies was determined by protein measurement and SDS-PAGE analysis.

The following cell lines were deposited with the American Type Culture Collection, Rockville, Md. 20852 (ATCC). These deposits were made under the provisions of the Budapest Treaty on the International Recognition of the Deposit of Microorganisms for purposes of Patent Procedure and the Regulations thereunder (Budapest Treaty). This assures maintenance of a viable culture for 30 years from the date of deposit. The cell lines will be made available by ATCC under the terms of the Budapest Treaty, and subject to an agreement between applicant and ATCC that assures unrestricted availability upon issuance of the pertinent U.S. patent. Availability of the deposited cell lines is not to be construed as a license to practice the invention in contravention of the rights granted under the authority of any government in accordance with its patent laws.

MECA-367, ATCC No. HB 8478, deposited Jul. 10, 1987; and MECA-79, ATCC No. HB 9479, deposited Jul. 10, 1987.

2. Functional assay of ability of antibodies to block lymphocyte-endothelial cell recognition in an in vitro lymphocyte-endothelial cell binding assay: The in vitro model of the interaction between lymphocytes and HEV has been previously described (Butcher, et al., *J. Immunol.*, supra and Jalkanen and Butcher, *Blood*, supra), but was slightly modified in this investigation to allow assessment of the blocking activity of MECA-89, MECA-367, and MECA-79. Briefly, the antibodies defining the HEV of mucosal or peripheral lymphoid tissues were preincubated on 12 μm thick, freshly cut, unfixed frozen sections of lymph nodes or Peyer's patches for 30 minutes at 7° C. Controls included an isotype-matched monoclonal antibody and medium alone. Antibodies were used at a concentration of 100 μg/ml, and 100 μl were applied to each section. Following this preincubation, the medium was removed from both experimental and control sections, and the lymphocyte-HEV binding assay was conducted. For the binding assay, mouse mesenteric node lymphocytes or selected lymphoid lines or lymphomas in RPMI 1640 containing 20 mM HEPES and 5% newborn or fetal calf serum were studied.

a. Standard assay conditions were: One hundred µl of a suspension of lymphocytes at $3\times10^7$ per ml in cell suspension medium (RPMI containing 25 mM/L HEPES, pH 7.3, and 5.0% fetal calf serum) were incubated in 12 µm fresh-frozen sections of three human lymph nodes in a wax pen circle (Martex, Tech Pen, Scientific Products, McGraw Park, Ill) 1.8 cm in internal diameter. Clumps were removed from the sample populations prior to assay by passing the cell suspension through monofilament nylon mesh (Sullivans, San Francisco, Calif.). The sections were rotated on a Tekpro-t (American Scientific Products, Sunnyvale, Calif.) shaker at 60–70 rpm for 30 minutes at 7° C. (¾" radius of rotation, horizontal motion). It is important to begin agitation prior to addition of sample cells. After incubation, the medium was removed by gently rapping the edge of the slide against an absorbent towel. Slides were then placed on edge in 1% glutaraldehyde (diluted from 49% stock, MCB, Manufacturing Chemists, Cincinnati, Ohio) in cold PBS and left overnight to fix adherent lymphocytes to the section.

b. Identification and counting of HEV-adherent lymphocytes: After incubation and fixation, nonadherent lymphocytes were rinsed off with a gentle stream of PBS, and the sections were examined with a 16x objective by darkfield illumination under PBS. Under these conditions, HEVs can be clearly distinguished from surrounding paracortex by a distinct dark line (the basement membrane) that delineates their characteristic round to elongated shape. Adherent lymphocytes appear as distinct bright circles lying above the plane of the tissue section. The number of lymphocytes bound to each HEV was recorded. For most experiments, six sections per sample were coded and counted single-blind. Areas with heavy nonspecific binding were not counted.

c. Data treatment: The mean number of cells bound to the individually scored HEVs and the standard error of the mean were calculated for each sample.

As shown in Table 2, MECA-79 inhibits the binding of lymphocytes to peripheral lymph node HEV by 95%, without affecting binding to HEV in the gut-associated Peyer's patches. Conversely, MECA-367 inhibits binding to Peyer's patch HEV by 90%, without influencing adherence to lymph node HEV. Control antibodies as well as MECA-89 were without significant effect. MECA-79 and -367 also block (with the same specificity) the binding of transformed lymphoid cell lines. Thus MECA-79 and MECA-367 inhibit tissue-specific lymphocyte endothelial cell interactions required for extravasation from the blood into peripheral lymph nodes or into mucosal Peyer's patches, respectively.

TABLE 2

ORGAN-SPECIFIC INHIBITION OF LYMPHOCYTE-HEV BINDING BY MONOCLONAL ANTIBODIES MECA-367 AND MECA-79

| TISSUE | ANTIBODY TREATMENT | CELLS/HEV (x ± SE) | BINDING AS % OF CONTROL |
|---|---|---|---|
| Peyer's Patches | Medium Control | 1.14 ± 0.06 | (100) |
| | MECA-367 | 0.11 ± 0.04 | 10* |
| | MECA-89 | 1.00 ± 0.17 | 88 |
| | IgG2a Control | 1.01 ± 0.12 | 89 |
| | MECA-79 | 1.09 ± 0.16 | 96 |

TABLE 2-continued

ORGAN-SPECIFIC INHIBITION OF LYMPHOCYTE-HEV BINDING BY MONOCLONAL ANTIBODIES MECA-367 AND MECA-79

| TISSUE | ANTIBODY TREATMENT | CELLS/HEV (x ± SE) | BINDING AS % OF CONTROL |
|---|---|---|---|
| | IgM Control | 1.18 ± 0.17 | 104 |
| Peripheral Lymph Nodes | Medium Control | 14.5 ± 1.4 | (100) |
| | MECA-367 | 15.9 ± 1.4 | 110 |
| | MECA-89 | 16.3 ± 1.6 | 112 |
| | IgG2a Control | 14.0 ± 1.7 | 92 |
| | MECA-79 | 0.77 ± 0.2 | 5* |
| | IgM Control | 13.8 ± 1.5 | 95 |

*P < 0.001 vs. other treatments

Antibodies capable of blocking lymphocyte HEV interaction in the in vitro assay were selected for subsequent in vivo studies. In addition, antibodies recognizing tissue-specific or inflammation-specific determinants on endothelial cells, whether or not they exhibited inhibition in the in vitro assay, were also selected for inhibition for in vivo studies when deemed appropriate. (For example, MECA-89 fails to inhibit lymphocyte-HEV interactions in vitro, yet blocks lymphocyte homing to mucosal Peyer's patches by 80% in vivo—see below. This antibody has been shown to bind the same mucosal endothelial cell molecule defined by the completely blocking antibody, MECA-367.)

3. Inhibition of in vivo homing:

a. In vitro labeling of normal lymphocytes with $^{51}$Cr: Normal mesenteric node lymphocytes were recovered from minced nodes that were gently pressed through metal gauze under frequent flushing with HBSS. Lymphocytes were washed, and labeled at $1\times10^7$ cells/ml using a modification of a standard technique (Butcher and Ford, Chapter 57, in *Handbook of Experimental Immunology*, Vol. 2, Weir and Herzenberg, Eds. 1986, 4th Edition, Blackwell Publishers). Briefly, cells were incubated with 100 Ci/ml sodium chromate ($Na_2^{51}CrO_4$, New England Nuclear, Boston, Mass.) for 1 hour, with mixing every 10–15 minutes at 37° C. in DMEM (Gibco) supplemented with 20 mM HEPES and 5% FCS. After labeling, the cells were centrifuged through a layer of FCS, and washed twice with HBSS prior to injection into animals.

b. In vivo homing: For the assessment of antibody blocking activity, mice received tail vein injections of either HBSS alone, MECA-367, MECA-89, MECA-79, or IgG2a control antibody Hermes-1 (1 mg doses were given). In some experiments, mice received two antibody injections, the first being one day before the assay, and the second, 4 hours before injection of labeled cells. In most experiments, mice received one antibody injection 4 hours before administration of labeled cells. $2\times10^7$ labeled cells bearing 385,000 cpm $^{51}$Cr were delivered in vivo by tail vein injection, and 1 hour after the administration of cells, animals were euthanized, various organs were harvested, and lymphocyte localization into the various tissues were determined by quantitating the $^{51}$Cr in each organ on a Packard gamma counter.

The results are presented in Table 3. MECA-367 and MECA-89 selectively inhibit lymphocyte extravasation into mucosal Peyer's patches, and MECA-79 inhibits lymphocyte localization to peripheral lymph nodes.

TABLE 3

In Vivo Blockade of Homing

| Antibody Treatment | Peripheral Lymph Node* | Mucosal Peyer's Patches | Spleen |
|---|---|---|---|
| Media Control | 11,500 ± 3545** cpm | 5468 ± 477 | 117,579 ± 16,179 |
| MECA-367 | 10,224 ± 1031 cpm (89)*** | 181 ± 36 (3) | 122,940 ± 16,543 (104) |
| MECA-89 | 11,107 ± 370 (97) | 1114 ± 98 (20) | 109,598 ± 9521 (93) |
| MECA-79 | 5743 ± 524 (50) | 5028 ± 1669 (92) | 139,709 ± 12,894 (119) |

*Axillary, brachial, inguinal
**Mean ± SE of cpm localized in organ 1 hour after injection of labeled lymphocytes
***Localization as percent of control cells

Identification of Endothelial Cell Antigen Defined by Antibodies MECA-367 and MECA-89

Mesenteric nodes from ten 12-week old Balb/c mice were minced and most lymphocytes were flushed away from stromal tissue by flushing with HBSS over a wire mesh. The crude stromal preparation was suspended in 30 ml and stromal tissue allowed to settle to further separate stroma from lymphocytes. The stromal preparation was washed once with HBSS and pelleted by centrifugation at 250 g for 7 minutes. The crude stromal isolate was lysed by addition of 10 ml of Tris lysis buffer (TLB; 2% NP-40, 150 mM sodium chloride, 1 mM MgCl$_2$, 0.02% NaN$_3$, and 10 µg/ml aprotinin, 10 µg/ml leupeptin, 10 µg/ml pepstatin, 1 mM PMSF, and 20 mM Tris-HCl pH 8.0), and incubated 90 minutes on ice. The lysate was then clarified by centrifugation for 15 minutes at 100,000 g.

Affinity columns were produced by conjugating MECA-367 antibody or control rat IgG2a (Hermes-1, of irrelevant specificity) antibody at 1–5 mg antibodies/ml packed beads to CNBr-activated Sepharose 4B beads per the manufacturers directions (Pharmacia, Sweden). The clarified lymph node stromal lysate was sequentially applied to 1 ml control antibody and 1 ml specific MECA-367 antibody columns at room temperature and 1 ml/minute. Both columns were washed extensively in wash buffer (0.1% NP-40, 500 mM NaCl, 50 mM Tris-HCl pH 7.4, 10 µg/ml leupeptin, 10 µg/ml pepstatin, 10 µg/ml aprotinin, and 1 mMPMSF) and separately eluted with 0.2 M acetic acid, 500 mM sodium chloride, 0.1% NP-40 solution. Ten fractions of 600 µl were collected, the pH was measured by standard pH paper and 1 M Tris-HCl, pH 8.0 was added to neutralize each fraction. Fractions 2–5 were pooled and concentrated by centrifugation with Centricon 10 microconcentrators (Amicon) to 200 µl. The eluate from the MECA-367 antibody column but not the control column contained the mucosa-specific endothelial determinant, as demonstrated by immunoblot analyses. Briefly, 2 µl of the concentrated eluates were applied to nitrocellulose paper (Bio-Rad Transplot) and allowed to dry. The nitrocellulose was blocked by incubation with 10% horse serum in TBST (10 mMTris-HCl pH 7.4, 150 mMNaCl, 0.5% Tween-20) for 30 minutes at room temperature. The nitrocellulose blots were then incubated at room temperature for 30 minutes with 100 µg/ml MECA-367 in TBST (or with control antibody Hermes-1), washed 3 times for 10 minutes each in TBST at room temperature, and incubated in second-stage indicator antibody, alkaline phosphatase-conjugated goat anti-rat IgG (Sigma, Catalog No. A-9645) at 1:200 for 30 minutes at room temperature with gentle shaking. The blots were washed 3 times as above and were developed by addition of AP substrate solution (100 mM Tris-HCl pH 9.5, 100 mM sodium chloride, 5 mM MgCl$_2$ containing 33 µl NBT (nitro blue tetrazolium, 50 mg/ml 70% dimethyl formamide) and 16.5 µl BCIP (5-bromo-4-chloro-3-indolyl phosphate, 50 mg/ml dimethyl formamide) per 5 ml solution). The reaction was terminated after 30 minutes by addition of 20 mM Tris-HCl, pH 7.4 and 5 mM EDTA. The eluate of the MECA-367 column, but not the control column contained material immunoreactive with MECA-367. This specific eluate also reacted with MECA-89, demonstrating that the MECA-367 antigen also bears the MECA-89 epitope. The control antibody Hermes-1 gave no signal in the immunoblot analyses of control or specific antibody column eluates. Western analyses, using sodium dodecyl sulfate/polyacrylamide gel electrophoresis (SDS-PAGE) and immunoblotting analysis were carried out to identify the molecular weight of the MECA-367 antigen. Fifty µl of the concentrated eluates from the control or specific antibody columns were mixed with an equal volume of Laemmli sample buffer (Laemmli, 1970, Nature 227:680) and applied to a 8% SDS-PAGE gel and electrophoresed under reducing conditions. The gel contents were then transferred electrophoretically to nitrocellulose (by electroblotting using a Bio-Rad Transblot apparatus in the presence of a glycine/methanol buffer as described by the manufacturer). The antigen was detected by immunologic analysis as described above for immunoblot analysis: first-stage antibody (MECA-367, or in control gel transfers, Hermes-1) was incubated with nitrocellulose blots at 100 µg/ml in 20 ml TBST at room temperature for 30 minutes. The filters were washed, exposed to second-stage antibody, and developed by the addition of AP substrate solution (see above). The procedure revealed the MECA-367 antigen to be a molecule of approximately 58–69 kD apparent molecular weight under these conditions of electrophoresis. MECA-89 reacted with the same band, confirming that the MECA-89 and MECA-367 epitopes are on the same mucosa-specific endothelial cell molecule.

Production of Antibodies Against Human Endothelial Cells Involved in Lymphocyte Traffic The same techniques are applicable to the production of antibodies to human endothelial cells involved in lymphocyte traffic. Two examples illustrate this point: First, monoclonal antibody MECA-79, described above and originally isolated as defining mouse lymph node high endothelial molecules for lymphocyte binding, has been found to cross-react antigenically and functionally (by binding to lymph node HEV and blocking lymphocyte binding to HEV) with human HEV. Secondly, a monoclonal antibody specific for human HEV, HECA-452, has been produced by immunizing rats with crude stromal preparations of human tonsils, using procedures paralleling those described in the foregoing examples.

Production of Monoclonal Antibody HECA-452, Specific for Human HEV

As a source for lymphoid tissue rich in HEV, tonsillectomy specimens were obtained through the Department of Pathology, Stanford University Medical Center. Fresh or stored frozen tissues were trimmed into pieces of about 0.5 cm³ and were squeezed on metal gauze under frequent flushing with RPMI 1640 medium (from Gibco; containing 20 mM HEPES, pH 7.3) to remove lymphocytes. Stromal remnants left on top of the screen were collected, and were homogenized in PBS in a ground glass homogenizer routinely used for preparing cell suspensions from lymphoid organs. The homogenate was centrifuged (200 xg, 10 minutes at 4° C.) and the pellet thoroughly mixed with Freund's adjuvant in a 1:1 ratio (final volume 1 ml), and used for immunization.

Three-to-four month old Wistar rats were immunized with 1 ml of the stromal preparation of tonsil (0.5 cm³/rat) in complete Freund's adjuvant intraperitoneally. About 3-4 weeks later the rats were boosted i.p. with a stromal preparation of tonsil in incomplete Freund's adjuvant.

Four days after boosting, rat spleen cells were fused with Sp2/0 mouse myeloma cells as above. Supernatants were screened for reactivity with HEV in frozen sections of human tonsil tissue by the immunoperoxidase technique described above. The hybridoma producing the HECA-452 antibody was subcloned by limiting dilution and expanded.

In immunoperoxidase staining of sections of lymphoid organs the HECA-452 antibody clearly stained all HEV observed in tonsils, lymph nodes, and gut-associated lymphoid tissue (GALT). The antibody was highly selective for the endothelium of HEV, staining the high endothelium intensely. In most studies, no other vessels were stained. In occasional hyperplastic tonsils, however, weak reactivity was observed with small venules around the periphery of organized lymphoid accumulations. The antibody exhibited no reactivity with the endothelium of capillaries, arterioles, or larger veins in lymphoid tissues, and failed to stain any vessel in thymus and spleen, lymphoid organs lacking functional HEV.

In addition to high endothelium, HECA-452 also stained a small population of cells scattered primarily within the T cell areas in lymphoid organs and also in the red pulp of the spleen. FACS analysis of peripheral blood and tonsil lymphocytes indicates that some T cells also react with HECA-452 (Picker et al. (1990) *Nature* 349:796-799; Picker et al., (1990) *Am. J. Pathol.* 136:1053-1068; Picker et al. (1990) *J. Immun.* 145:3247-3255; and see below).

HECA-452+ vessels were absent in sections of numerous normal non-lymphoid tissue specimens, except in the setting of dense infiltration by chronic inflammatory cells, especially lymphocytes.

SKIN VASCULAR ADDRESSIN

In order to demonstrate the association of ELAM-1 with cutaneous trafficking T-lymphocytes, the following study was carried out.

Materials and Methods

Tissues and Cell Preparation:

Samples of snap-frozen tissues for immunostaining were obtained from the Department of Pathology's frozen tissue bank at Stanford University, except for synovial tissue and salivary gland specimens which were provided by Drs. S. Jalkanen (University of Turku, Finland), and N. Wu (Stanford University), respectively. Diagnostic classification of all specimens was done on the basis of standard pathologic, and as appropriate, clinical criteria.

The distribution of ELAM-1 reactivity on vessels in these chronic inflammatory lesions was analysed using a three-stage immunoperoxidase technique (see below). The skin lesions studied included five cases of psoriasis, four of allergic contact dermatitis, three of lichen planus, two of lymphoid hyperplasia in the skin, two of nonspecific chronic dermatitis, and one each of pityriasis lichenoides et varioliformis acuta, granuloma annulare, cutaneous drug eruption, and pityriasis rubra pilaris. Non-cutaneous chronic inflammatory lesions included ten from the gastrointestinal tract (five from the stomach, small bowel or colon, three from salivary glands, and two from liver), four inflamed synovia (rheumatoid arthritis), four from the lung, two each of mycocardium and nasopharynx, and one each of the kidney, bladder, thyroid and subcutaneous soft tissues. ELAM-1 reactivity was defined by monoclonal antibodies CL2 and CL3, and compared with a class-matched negative control on two to six levels through the tissue block for each specimen. Reactivity for each specimen was graded on the most-positive vessels identified, if any, as intense, moderate or weak (barely detectable). The CL2 and CL3 antibodies were raised against interleukin-1-activated human umbilical vein endothelial cells and have similar patterns of staining reactivity and anti-adhesion activity as previously reported anti-ELAM-1 monoclonal antibodies (Sakstein et al., (1988) *J. Invest. Derm.* 91:423-428) including the recognition of COS cells transfected with ELAM-1 cDNA but not control cDNA. For further discussion see Picker et al., (1991) *Nature* 349:796-799.

Adherence Assay of PBMC Binding to ELAM-1 Transfected COS Cells:

COS cells were transfected by the standard DEAEdextran technique, as previously described. ELAM-1 cDNA in the cDM8 expression vector was provided by B. Seed (Harvard University) and was also derived by polymerase-chain-reaction amplification from a stimulated human umbilical vein endothelial cells (HUVEC) cDNA library using appropriate oligonucleotides based on the published ELAM-1 cDNA sequence (Bevilacqua, et al., (1989) *Science* 243:1160–1165). COS cells transfected with either clone stained specifically with anti-ELAM-1 monoclonal antibody and gave similar results in adhesion assays. Typically, more than 40% of the cells were transfected, as judged by immunofluorescence with the appropriate monoclonal antibody. As a control, COS cells were 'mock'-transfected under the same conditions as above, except that no DNA was added. After transfection, the COS cells were incubated for 24-48 h, collected, pooled and replated (to ensure an even distribution of transfectants among different plates), and were used for adhesion assays 24 h later. PBMC or PMN were freshly isolated by ficoll-hypaque density centrifugation and dextran sedimentation, respectively, and suspended at in HEPES-buffered DMEM medium with no serum. Cell suspension (1 ml) with $3-5\times10^5$ cells was added to each 3.5-cm plate (in triplicate) containing control or ELAM-1-transfected COS cells. The plates were gently rotated (60 rpm) on a gyrotory shaker for 30 min at 25° C., washed four times by aspirating and then gently filling each plate with 2 ml DMEM, and then fixed with 1% glutaraldehyde in Hanks Balanced Salt Solution. For antibody blocking experiments, ELAM-transfected COS cells were pretreated with 30 μg ml$^{-1}$ each of the anti-ELAM monoclonal antibodies CL2 and 1.2B6 (Wellicome et al., (1990) *J. Immun.* 144:2558–2565) before the binding assay.

Assay of PBMC Subset Binding to ELAM-1 Transplants:

Adhesion assays were performed as described above, except that $4\times10^6$ PBMC in 2 ml HEPES-buffered DMEM were added to 6-cm plates containing the ELAM-1-transfected COS cells. Non-adherent cells were exposed to three cycles of incubation on ELAM-1 transfectants with aliquots from each cycle being saved for analysis. The adherent cells from each round were examined visually and then collected by addition of $Ca^{2+pk}$ $^{/Mg2+}$-free HBSS containing 5 mM EDTA and 5 mM EGTA (recovery>90%). Binding of mononuclear cells to plastic under the conditions of this assay was negligible. In some experiments, an aliquot of the collected adherent cells from a single round of adherence was subjected to a second round of adherence to transfected COS cells to further enrich for ELAM-binding monomuclear cells. Input, non-adherent and adherent cells were stained for single- or two-color immunofluorescence (FITC versus phycoerythrin) and analysed by flow cytometry as previously described.

MABs:

The monoclonal antibodies used included T/S2.9 (anti-LFA-3/CD58), HECA-452 (anti-CLA; see Picker et al. (1990) *Nature* 349:796–799 and Picker et al. (1990) *Am. J. Pathol.* 136:1053–1068), Ber ACT8 (anti-MLA), Leu 2 (CD8; all Leu monoclonal antibodies from Becton-Dickinson Immunocytometry Systems, San Jose, Calif.), Leu 3 (CD4), Leu 4 (CD3), Leu 5 (CD2), Leu 8 (anti-LECAM-1, the peripheral lymph node homing receptor; (Picker et al. (1990) *J. Immun.* 145:3243–3255))) Leu 12 (CD19), Leu 14 (CD22) and Leu M3 (CD14). All antibodies were used at saturating concentrations as determined by both FACS analysis and immunoperoxidase techniques.

Flow Cytometry:

For one-color immunofluorescence, cell populations ($1 \times 10^6$ cells/test) were incubated with a primary unconjugated mouse mAb, washed twice in PBS, incubated with a Phycoerythrin (PE)-conjugated anti-mouse IgG (Tago, Burlingame, Calif.), and washed with PBS. For two-color immunofluorescence, cells were additionally blocked (10 minutes) and washed with 5% normal mouse serum (NMS) plus 5% normal rat serum (NRS) in PBS, and then incubated with FITC-HECA-452 or control mAb. All antibody incubation periods were for 30 minutes at 4° C. in the presence of 0.2% sodium azide. After washing twice, the stained cells were either analyzed immediately or fixed in 1% paraformaldehyde in PBS and saved at 4° C. for later analysis. In some two-color experiments, unconjugated HECA-452 or control mAb were used as initial antibodies followed by staining with PE-conjugated anti-rat IgG (Tago, heavy and light chain reactive), and then FITC-labelled mouse mAbs. These two staining techniques gave identical results.

Flow cytometry analysis was performed on a FACStar (Becton Dickinson Immunocytometry Systems, Mountain View, Calif.) equipped with an argon laser which was operated at 488 nm. The FITC and PE emissions were collected with 530/30 and 585/42 band pass filters, respectively. All data were collected in list mode, ungated. For analysis, gates were drawn to include the whole population excluding only doublets and larger cell aggregates, or were drawn around the lymphocyte, monocyte, and granulocyte regions as appropriate. Data analysis was done with Consort 30 software. The delineation and quantitation of positively stained populations (i.e., placement of marker quadrants) was based on samples stained with isotype-matched antibody controls (positive quadrants with <0.7% cells in control plots).

Binding of Isolated CLA$^+$ T cells to ELAM-1 Transfectants:

The ELAM-1 adhesion assay was performed as described above comparing identical number of PMN, PBMC, CLA$^+$ T cells and CLA$^-$ T cells ($3-5 \times 10^5$ cells per 3.5-cm plate of subconfluent ELAM-1-transfected COS cells). Highly purified CLA$^+$ and CLA$^-$ T cells were obtained using a FACSTAR fluorescence activated cell sorter (Becton-Dickinson Immunocytometry Systems), using techniques previously described (Terstappen et al. (1990) *J. Leuk. Biol.* 48:138–148) (Preliminary studies indicated that HECA-452 mAb did not block ELAM-1 binding in this assay). Binding was quantitated by the counting of bound cells per ×200 field; 10 random fields were counted per plate and triplicate plates were analysed for each cell type. Examination of the plates before washing revealed that more than 90% of added PMN and CLA$^+$ T cells bound to the ELAM-1 transfected COS cells during the assay, compared with less than 10% binding by CLA$^-$ T-cell.

Tissue Section Immunostaining:

Serial, acetone-fixed, air-dried cryostat sections (5–6 μm) were prepared from snap-frozen tissue specimens and stained using a 3-stage immunoperoxidase technique. Sections were incubated serially (45 minutes in a humidified chamber with PBS washes in between) with primary mAbs, biotinylated secondary antibodies (goat anti-rat IgM (Kirkegaard & Perry Labs, Gaithersburg, Md.), or horse anti-mouse IgG (Vector Labs, Burlingame, Calif.)) as appropriate for the primary mAb, horseradish peroxidase-conjugated Streptavidin (Zmed), and then developed with 0.05% 3,3-diaminobenzidine (Sigma) and 0.009% hydrogen peroxide in 50 mMTris/HCl (pH 7.5) for 10 minutes. Second and third stages included 5% normal human serum (NHS) to decrease background. After darkening the reaction with 0.5% copper sulfate in 0.9% NaCl for 5 minutes, sections were counterstained with 2% methylene blue, dehydrated, and coverslipped.

RESULTS

ELAM-1 Selectively Binds Skin Associated Memory T cells that Express the Cutaneous Lymphocyte Antigen Pooled Ficoll-isolated peripheral blood mononuclear cells (PBMC) were incubated on COS cells transfected with ELAM-1 cDNA in the pCDM8 expression vector. Although the PBMC bound less well than neutrophils, as reported in the literature, significant numbers of mononuclear cells adhere to the ELAM-1 transfectants, but not to control mock-transfected COS cells. PBMC were incubated on ELAM-1 transfected COS cells and the non-adherent cells were rinsed off by gentle washing. The non-bound cells were incubated on a second and subsequent third set of ELAM-1 transfectants. Aliquots of the non-adherent fraction were taken after each incubation for FACS analysis. The adherent cells, (those that adhere were released following addition of 5 mM EDTA+ 5 mM EGTA and gentle pipeting), were pooled from each of the plates. Aliquots of the starting PBMC population, of the non-adherent fractions, and of the pooled bound cells were stained with monoclonal antibodies and analyzed by flow cytometry to define unique memory and virgin lymphocyte subsets.

The following markers were studied: LFA-3, expressed at high levels by memory T lymphocytes but low or absent on virgin T lymphocytes; Leu-12 or Leu-14 as markers of B cells; the peripheral lymph node homing receptor LECAM-1 (Dreg-56, Leu-8, TQ1, Lam-1, etc.), a lymphocyte receptor for peripheral lymphold HEV that is expressed by virgin B and T lymphocytes, but divides memory T lymphocytes into positive and negative subsets. In addition, markers that define unique skin associated or mucosa-associated lymphocyte populations were employed. The cutaneous lymphocyte antigen (CLA), defined by mAb HECA-452 is expressed by 80–90% of T cells in an inflamed skin and 10–15% of circulating T memory cells in peripheral blood, but is absent from most T cells in organized lymphoid tissues and in extracutaneous sites of inflammation (Picker, et al. (1990) *Nature* 349:796–799; Picker, et al. (1990) *Am. J. Pathol.* 136:1053–1068; and Picker et al. (1990) *J. Immun.* 145:3247–3255). The mucosa-associated lymphocyte antigen (MLA) (Picker et al. (1990) *Nature* 349:796–799 and Picker, et al. (1990) *J. Immun.* 145:3247–3255), defined here by mAb BerAct8 is expressed by gut intraepithelial leukocytes in most lamina propria T cells and marks a 1–3% subset of circulating memory T cells in the blood. Finally, light scatter parameters and/or LeuM3 staining were used to identify monocytes.

The CLA$^+$ skin-associated memory T cell subset was dramatically depleted from PBMC by incubation on ELAM-1$^+$ COS cells and correspondingly enriched in the ELAM-1 binding fraction. The percentage of CLA$^+$ cells in PBMC, which averaged 12% of the starting population, was typically reduced by >50% following one round of adherence and almost completely depleted after 3 rounds (residual percentage of CLA$^+$ cells 1–4%, N=6). On the other hand, there was a striking 3–4-fold enrichment in the frequency of CLA$^+$ cells in the pooled bound fractions, which were typically 50% CLA$^+$. None of the other antigenically defined lymphocyte subsets studied was substantially or reproducibly enriched or depleted by the incubations, although there was a slight increase in MLA$^+$ cells in the nonbound fraction and in LFA-3+ cells in the adherent population, consistent with the fact that CLA$^+$ T cells are LFA3+ and MLA$^-$ In separate experiments, CLA$^+$ and CLA$^-$ peripheral blood T cells were separated by fluorescence activated cell sorting and incubated on ELAM-1 transfectants. The CLA$^+$ population bound almost quantitatively to the transfected cells, whereas the sorted CLA$^-$ population bound only poorly. The CLA$^+$ population appears to bind at least as well as isolated neutrophils, incubated in parallel in separate wells.

ELAM-1 is Preferentially Expressed in Cutaneous Sites Chronic Inflammation

Immunohistologic analysis of biopsies of chronically inflamed skin from patients with a variety of dermatologic disorders revealed intense ELAM-1 expression by venules. Among non-cutaneous lesions examined, moderate ELAM-1 staining was seen in some lesions. The majority of biopsies of chronically inflamed mucosal tissues (intestine, stomach, etc.) and other sites contained no venules expressing detectable ELAM-1, but weak staining was observed occasionally. Of particular interest was the observation that both ELAM-1$^+$ venules and CLA$^+$ T-cells were both rare in or absent in inflamed synovium from patients with rheumatoid arthritis.

HUMAN PERIPHERAL LYMPH NODE VASCULAR ADDRESSIN AND LECAM-1

Materials and Methods

Immunoisolation of PNad.

PNad (the MECA-79 antigen), and control membrane glycoproteins LECAM-1 and H-CAM (the Hermes antigen or CD44, Jalkanen et al., (1986) *Eur. J. Immunol.* 16:1195–1202 were isolated from human tonsils using a two-step procedure. Briefly, NP-40 tissue extracts were prepared as previously described (Streeter et al., *Nature* 331:41–46 (1988)); Nakache et al., *Nature* 337:179–181 (1988)), then passed over wheat germ agglutinin-coupled agarose columns (Vector). Material eluting with 0.5 M N-acetylglucosamine was then passed sequentially through 2 ml affinity columns of rat IgMmAb control and Hermes-1 (anti-H-CAM or CD44) (Jalkanen et al., (1986) supra) or DREG-56 (anti-LECAM-1) Kishimoto et al., PNAS, USA 87:2244–2248 (1990) and then MECA-79 coupled to Sepharose 4B (Pharmacia). The column wash and elution conditions with β-octylgluco-side-containing wash buffer were as previously described for the isolation and functional reconstitution of the mucosal addressin (Nakache et al., (1988) supra). To assess the purity, an aliquot of each of the column eluates was iodinated by standard methods (Iodogen, Pierce), desalted to remove free iodine, and analyzed by SDS-PAGE followed by autoradiography. Samples run on SDS-PAGE and stained with silver, show the same pattern of species. Western blots on immunoisolated PNAd were performed as previously described (Streeter et al., (1988) supra), except that the second stage employed was alkaline phosphatase-conjugated rabbit anti-rat IgG (H+L) from Tago (Burlingame, Calif.). Preliminary studies with Western analysis confirmed that all detectable MECA-79-reactive species in tissue lystates were bound by wheat germ agglutininin.

Binding of lymphocytes and cell lines to PNAd.

Samples of human PNAd or control proteins were absorbed onto glass wells of slides (LabTek) by dilution in Dulbecco's Modified Eagles Medium (DMEM, Applied Scientific), followed by a 2 hour incubation at room temperature. After blocking with complete medium (CM, 10 mM HEPES, 5% newborn calf serum (Gibco) in DMEM), human peripheral blood mononuclear cells (PBMC), or PLN lymphocytes from normal BALB/c mice (1.5×10$^6$/0.15 ml CM) were applied to each well. After incubation for 20 minutes at RT on a rotating shaker (50 rpm), the tops of the wells were removed and the slides washed by dipping twice into coplin jars of DMEM and then fixed by incubation in 1.5% glutaraldehyde (Kodak) in DMEM for 1 hour. PBMC were prepared by 1 g sedimentation of red blood cells with Dextran T500 (Pharmacia) and then centrifugation of the white blood cells on Ficoll-histopaque (Sigma Histopaque 1077) and then 25% Percoll (Pharmacia) gradients to separate mononuclear cells from polymorphonuclear leukocytes and platelets. Most PNAd adherent cells were lymphocytes, as assessed morphologically and by Wrights stain. Both human and mouse lymphocyte interactions with human PNAd were studied as the tissue-specificity of lymphocyte-HEV interactions is retained across species barriers. [Mouse lymphocyte and lymphocyte cell lines can bind to and discriminate between human PLN HEV and appendix HEV with the same specificity as do human lymphocytes, and human lymphocytes adhere to murine PLN HEV and mucosal HEV via the same distinct mechanisms as do mouse lymphocytes (Wu et al., (1988) *J. Cell. Biol.* 107:1845–1851)]. Binding of cell lines was carried out as described for lymphocytes. Lymphocyte cell lines tested which bind well to PLN HEV include the human Jurkat JS-978 (Stoolman and Ebling, (1989) *J. Clin. Immun.* 84:1196–1205) and mouse 38C13 (Gallatin et al., (1983) *Nature* 304:30–34) cell lines. The mouse cell line L1-2 does not bind either PLN or mucosal HEV; and mouse lines TK1 and TKJ43 avidly bind mucosal HEV, but do not bind well to PLN HEV (Butcher et al., (1980) Eur. J. Immunol.

10:556–561; Gallatin et al., (1983) *Nature* 304:30–34). L1-2 cells transfected with mouse LECAM-1 or cDNA, as described below, were also tested. The amount of PNAd added per well ranged from approximately 10 ng-100 ng (roughly estimated from comparison on silver stained gels). In all of the studies presented here, the amount of PNAd added per well was limiting, as increasing the amount of PNAd added per well led to increased lymphocyte attachment. In contrast, increasing the amount of control proteins added to each well (either H-CAM or LECAM-1) never resulted in lymphocyte attachment.

For some binding experiments, the wells containing PNAd were washed and treated either with mAbs MECA-79 or control rat IgM mAb HECA-452 (Duijvestijn et al., (1988) *Am. J. Path.* 130:147–155) (200 µg/ml in CM) for 30 minutes and then washed in CM prior to the addition of lymphocytes. Alternatively, wells containing PNAd were treated with *Vibrio cholera* neuraminidase 5mU/ml (Calbiochem) in 50 mM NaH$_2$PO$_4$, pH 6.0, 2 mM CaCl$_2$ for 30 minutes prior to washing with CM, and subsequent addition of lymphocytes. Similar results were obtained using the neuraminidase from *Arthrobacter ureafaciens*.

The calcium dependence of the interaction of lymphocytes with PNAd was tested by performing the assay with lymphocytes suspended in Hank's balanced salt solution without calcium or magnesium (HBSS, Applied Scientific) containing 0.5 mM EGTA or HBSS containing 0.5 mM EGTA and 5 mM CaCl$_2$.

To test anti-lymphocyte mAbs, human or mouse lymphocytes were preincubated with 100 µg/ml/10$^7$ cells of the mAbs DREG-56 (anti-human LECAM-1) (Kishimoto et al., (1990) supra), Hermes-3 (anti-human H-CAM or CD44) (Jalkanen et al., *J. Cell Biol.* 105: 983–990), MEL-14 (anti-mouse LECAM-1) (Gallatin et al., (1983) supra), R1/2 (anti-mouse VLA-4 αchain, LPAM) (Holzmann et al., (1989) *Cell* 56:37–46), 30G12 (anti-mouse T200) (Ledbetter and Herzenberg, (1982) *Immunol. Rev.* 47:63–90), FD441.8 (anti-mouse LFA-1α, CD11a) (Sarmiento et al., (1982) *Immunol. Rev.* 681:135–169), MJ-64 (anti-mouse CD44), or media (10$^7$ cells/ml) for 30 minutes and then washed prior to the assay.

Construction of cell lines permanently transfected with LECAM-1

A cDNA clone encoding LECAM-1 was obtained from a mouse mesenteric lymph node library by polymerase chain reaction amplification. The LECAM-1 gene was inserted downstream of the hCMV promoter in pMRB101 (a derivative of EE6 which contains the *E. coli* gpt gene) (Mulligan and Berg, (1981) *Mol. Cell Biol.* 1:449–459); (Stephens and Cockett, (1989) *N.A.R.* 17:7110). DNA was introduced into L1-2 cells by electroporation (250 volts, 1180 µFarads) and the cells selected for resistance to mycophenolic acid. A population of cells staining brightly with MEL-14 were selected by fluorescence activated cell sorting and cloned by limiting dilution. These cells, L1-2/pMRB112 (L1-2$^{LECAM-}$$_1$) and cells transfected with the parent vector alone, L1-2/pMRB101 (L1-2$^{vector}$) were tested for binding to PNAd as described above, except that slides with cells bound were placed directly into fixative without washing. Except for LECAM-1 expression, the phenotypes of L1-2$^{LECAM-1}$ and L1-2$^{vector}$ cells are similar (T200$^+$, LFA-1$^+$, and CD44$^-$). In addition, the L1-2 cells transfected with LECAM-1, but not the parent cell line or cells transfected with the vector alone, bind PLN HEV in frozen sections.

RESULTS

Immunoprecipitation of PNAd

Immunoisolated PNAd, prepared by mAb affinity chromatography from extracts of human tonsil and iodinated, consists of a predominant polypeptide migrating at approximately 105 kD, and several less intense bands in 10% SDS-PAGE gels. The 105 kD species is also the predominant band seen in gels stained with silver, although in Western blots, additional bands at 65, 90, 150 and 200 kD are detected by MECA-79 (note that the smallest immunoprecipitated band of 45 kD is not recognized by MECA-79 by Western).

Isolated PNAd is an Adhesion Molecule for Lymphocytes

The MECA-79 antigen, PNAd, could direct lymphocyte extravasation either by binding circulating lymphocytes, or by a less direct mechanism such as activation of adhesion molecules for distinct HEV ligands. PNAd was isolated from human tonsils by sequential wheat germ agglutinin and antibody affinity chromatography and adsorbed onto glass slides. PNAd coated wells bound lymphocytes avidly. In contrast, lymphocytes bound poorly to wells coated with serum or with control membrane proteins, including human CD44, murine CD44 and mouse or human LECAM-1 homing receptors. Pretreatment of the PNAd-coated wells with mAb MECA-79 blocked lymphocyte attachment, while control antibodies had no effect on binding, confirming the specificity of the interaction.

Lymphocytes-Binding Ability of PNAd is Calcium-Dependent and Abrogated by Neuraminidase Treatment Carbohydrate determinants on PLN HEV have previously been implicated in lymphocyte attachment (Stoolman et al., (1987) *J. Cell Biol.* 99:1535–1540; (1987) *Blood* 70:1842–1850); Rosen et al., (1985). *Science* 228:1005–1007; (1989) *J. Immunol.* 142:1895–1902; Yednock et al., (1987) *J. Cell Biol.* 104:725–731). Certain anionic mono- and polysaccharides block lymphocyte attachment to PLN HEV in frozen sections (Stoolman et al., (1984) supra; (1987) supra; Yednock et al., (1987) supra). In addition, neuaminidase-treated PLN frozen sections do not support lymphocyte binding and neuraminidase treatment in vivo selectively blocks lymphocyte trafficking to PLN (Rosen et al., (1985) supra; (1989) supra). These effects could be due to charge effects on HEV, alteration of accessory mechanisms, or a direct effect on the HEV ligand. Treatment of immobilized PNAd with *Vibrio cholera* neuraminidase completely prevents lymphocyte binding. The inclusion of the sialidase inhibitor sialyllactose blocks the effect of the neuraminidase. This suggests that the ability of neuraminidase to block lymphocyte-HEV interactions is due to a direct effect on PNAd itself and that the interaction of lymphocytes with PNAd involves sialic acid residues. Interestingly, the MECA-79 epitope on PNAd is not affected by neuraminidase treatment.

Like lymphocyte attachment to HEV in PLN frozen sections, binding of lymphocytes to PNAd requires calcium, as preincubation of lymphocytes with EGTA inhibits their ability to bind isolated PNAd, while addition of calcium restores it.

PNAd Selectively Binds Lymphoid Cells That Can Bind to PLN HEV.

As the original identification of tissue-specific lymphocyte-HEV interactions was based on lymphoid cell lines of restricted binding specificities, we next compared the binding of cell lines that bind well to PLN HEV with that of cells that bind selectively to mucosal HEV, or cell lines which do not bind HEV. Two variants of the human Jurkat T cell line (provided by Lloyd Stoolman, U. Michigan) have been generated which differ dramatically in their expression of LECAM-1 and their capacity to adhere to PLN HEV (Stoolman and Ebling, (1989) supra). Only the high-binding cell line JS-978, which expresses high levels of LECAM-1, was able to adhere to isolated PNAd. The mouse lymphoma cell line, 38C13, an avid PLN HEV-selective binder (Gallatin et al., (1983) supra) which expresses high levels of mouse LECAM-1, also bound well to PNAd. In contrast, cell lines which express little if any LECAM-1, including the mucosal HEV-binding cell lines TKJ43 and TK1 and the HEV non-binding L1-2 (Butcher et al., (1980) supra; Gallatin et al., (1983) supra) cell line, did not bind to isolated PNAd, although in parallel experiments, TKJ43 and TK1 bound well to isolated mucosal addressin. These experiments demonstrate the specificity of PNAd for lymphocyte cell lines which express high levels of LECAM-1 and bind PLN HEV.

PNAd is a Countereceptor for LECAM-1.

Lymphocyte interactions with PLN HEV involve the peripheral lymph node homing receptor LECAM-1, defined by the monoclonal antibodies MEL-14 in the mouse and DREG-56, Leu-8 and others in the human (Gallatin et al., (1983) supra; Tedder et al., (1989) *J. Exp. Med.* 170:123–133: Camerini et al., (1989) *Nature* 280:496–498; Kishimoto et al., (1990) *PNAS USA* 87:2244–2248). Anti-LECAM-1 antibodies that inhibit lymphocyte-HEV interactions were tested for their ability to block lymphocyte binding to isolated human PNAd. Human lymphocyte binding to PNAd was completely blocked by pretreatment of the cells with DREG-56, and mouse lymphocyte binding was blocked by pretreatment with MEL-14. Binding was not inhibited by antibodies against the leukocyte common antigen, T200 (CD45), or against mouse or human CD44, including Hermes-3 which blocks human lymphocyte attachment to PP HEV (Jalkanen et al., (1987) *J. Cell Biol.* 105:983–990). Antibody to LFA-1 (CD11a/CD18) had a slight but reproducible blocking effect on binding to PNAd. Antibody R1/2 to the mouse integrin $\alpha_4$ chain, which inhibits lymphocyte binding to Peyer's patch but not PLN HEV in vitro (Holzmann et al., (1989) supra), also failed to influence binding to purified PNAd. In contrast to its inhibitory effect on binding to PNAd, MEL-14 had no effect on mouse lymphocyte adhesion to purified MAd. The nearly complete inhibition of PNAd binding by antibodies to LECAM-1 suggests that LECAM-1 either binds PNAd or is physically or functionally associated with a PNAd receptor on lymphocytes.

To examine the LECAM-1-PNAd interaction directly, the mouse pre-B cell line, L1-2, (which does not express LECAM-1, (Gallatin et al., (1983) supra), was transfected with cDNA encoding mouse LECAM-1 and the transfectants tested for their PNAd-binding capacity. L1-2 cells transfected with cDNA containing the LECAM-1 gene L1-2$^{LECAM-1}$ but not L1-2 cells transfected with the vector alone, L1-2$^{vector}$, bound specifically to isolated PNAd absorbed onto glass slides. These results indicate that the peripheral lymph node addressin is a ligand for LECAM-1, the peripheral lymph node homing receptor.

The evidence provided above demonstrates that the PNAd mediates lymphocyte attachment through LECAM-1 and supports a role for neuraminidase-sensitive sialic acid residues. A number of glycoprotein species of distinct molecular weights bear the PNAd defining mAb MECA-79 epitope; the predominant indicated species is about 105 kD in silver stained or iodinated preparations. In the mouse, MECA-79 recognizes a similar pattern of species by Western blot, predominant species gp90 and gp115, a minor 65 kD species and additional species of 75, 170, and 200. A 50 kD species was detected by incorporating $^{35}SO_4$ (metabolically labeled by mouse lymph node fragment incubation) and serves as a ligand for LECAM-1. The results support the conclusion that the MECA-79 and LECAM-1 binding ability, and, by analogy, other pairs of homing receptors and addressins, may be determined by unique PLN post-capillary venule specific glycosyltransferases or other posttranslational modification that can attach to more than one post-capillary venule surface acceptor molecule binding site for LECAM-1 and mAb MECA-79.

The above results demonstrate the role played by addressins in the trafficking of leukocytes, particularly lymphocytes, to various sites in the body. Since this trafficking can affect a wide variety of conditions, in many cases adversely, the ability to modulate such trafficking can be of substantial therapeutic value. In addition, by providing opportunities to direct particular agents to sites associated with inflammation, one can provide for either diagnosis or therapy at such site, can monitor events, so as to enhance the understanding of various inflammatory diseases, as well as the process of transfer from the vascular system to sites of inflammation. By being able to direct specific molecules to sites associated with inflammation, one can also evaluate the extent and degree of inflammation, changes in the course of inflammation, and the like.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of modulating leukocyte extravasation by inhibiting the binding of leukocytes to the peripheral lymph node addressin (PNAd) on endothelial cells comprising administration in a pharmaceutically acceptable vehicle of a monoclonal antibody selected from the group consisting of MECA-79, and a monoclonal antibody which binds to the same antigen as MECA-79.

2. A method of modulating leukocyte extravasation by inhibiting the binding of leukocytes to the peripheral lymph node addressin (PNAd) on endothelial cells comprising administration in a pharmaceutically acceptable vehicle of a monoclonal antibody fragment of an antibody selected from the group consisting of MECA-79, and a monoclonal antibody which binds to the same antigen as MECA-79.

3. The method of claim 1 or 2, wherein lymphocyte extravasation into peripheral lymph node is selectively inhibited.

4. A method of modulating leukocyte extravasation by inhibiting the binding of leukocytes to the mucosal addressin (MAd) on endothelial cells comprising administration of a monoclonal antibody selected from the group consisting of MECA-367 and a monoclonal antibody that binds to the same antigen as MECA-367.

5. A method of modulating leukocyte extravasation by inhibiting the binding of leukocytes to the mucosal addressin (MAd) on endothelial cells comprising administration of a monoclonal antibody fragment of an antibody selected from the group consisting of MECA-367 and a monoclonal antibody that binds to the same antigen as MECA-367.

6. The method of claim 4 or 5, wherein lymphocyte extravasation into mucosal Peyer's patches is selectively inhibited.

* * * * *